US009895678B2

(12) United States Patent
Pohl et al.

(10) Patent No.: US 9,895,678 B2
(45) Date of Patent: Feb. 20, 2018

(54) CATALYST AND METHOD OF MANUFACTURE

(71) Applicant: JOHNSON MATTHEY PUBLIC LIMITED COMPANY, London (GB)

(72) Inventors: Joachim Pohl, Bergen (DE); Aalbert Zwijnenburg, Doetinchem (NL)

(73) Assignee: Johnson Matthey Public Limited Company, London (GB)

( * ) Notice: Subject to any disclaimer, the term of this patent is extended or adjusted under 35 U.S.C. 154(b) by 549 days.

(21) Appl. No.: 14/388,862

(22) PCT Filed: Mar. 28, 2013

(86) PCT No.: PCT/GB2013/050839
§ 371 (c)(1),
(2) Date: Sep. 29, 2014

(87) PCT Pub. No.: WO2013/144650
PCT Pub. Date: Oct. 3, 2013

(65) Prior Publication Data
US 2015/0094499 A1    Apr. 2, 2015

(30) Foreign Application Priority Data
Mar. 30, 2012   (GB) .................... 1205764.2

(51) Int. Cl.
| *B01J 23/72*  | (2006.01) |
| *B01J 21/12*  | (2006.01) |
| *C07C 29/147* | (2006.01) |
| *B01J 37/00*  | (2006.01) |
| *C10G 35/06*  | (2006.01) |
| *C10G 49/02*  | (2006.01) |
| *C10G 3/00*   | (2006.01) |
| *C11C 3/12*   | (2006.01) |
| *C07C 29/149* | (2006.01) |
| *B01J 35/00*  | (2006.01) |
| *B01J 35/02*  | (2006.01) |
| *B01J 35/10*  | (2006.01) |

(52) U.S. Cl.
CPC .............. *B01J 23/72* (2013.01); *B01J 21/12* (2013.01); *B01J 37/0036* (2013.01); *C07C 29/147* (2013.01); *C07C 29/149* (2013.01); *C10G 3/48* (2013.01); *C10G 35/06* (2013.01); *C10G 49/02* (2013.01); *C11C 3/126* (2013.01); *B01J 35/002* (2013.01); *B01J 35/023* (2013.01); *B01J 35/1019* (2013.01); *Y02P 30/20* (2015.11)

(58) Field of Classification Search
CPC . B01J 21/06; B01J 21/063; B01J 21/08; B01J 21/12; B01J 23/72; B01J 35/1019; B01J 35/1023; B01J 35/1028; B01J 35/023; B01J 35/026
See application file for complete search history.

(56) References Cited

U.S. PATENT DOCUMENTS

| 4,597,908 A | 7/1986 | Lok et al. |
| 6,080,699 A | 6/2000 | Pohl |
| 6,306,795 B1 * | 10/2001 | Ryan ........................ B01J 23/72 423/604 |
| 6,313,358 B1 * | 11/2001 | Breitscheidel ........... B01J 23/72 560/191 |
| 2009/0312588 A1 | 12/2009 | Hatscher et al. |
| 2013/0123550 A1 | 5/2013 | Ma et al. |

FOREIGN PATENT DOCUMENTS

| CN | 101489671 | 7/2009 |
| DE | 43 08 120 | 9/1993 |
| DE | 196 11 132 | 9/1997 |
| EP | 0 145 094 | 6/1985 |
| EP | 2 586 528 | 5/2013 |
| KR | 20030076851 | 9/2003 |
| WO | 9009846 A1 | 9/1990 |

OTHER PUBLICATIONS

Chinese Office Action dated Jan. 15, 2016; Application No. 201380020993.2.
International Search Report dated Jul. 16, 2013, corresponding to PCT/GB2013/050839.
British Search Report dated Jul. 30, 202, corresponding to the Foreign Priority Application No. GB1205764.2.

* cited by examiner

*Primary Examiner* — Jun Li
(74) *Attorney, Agent, or Firm* — Baker & Hostetler LLP

(57) ABSTRACT

A method for making a solid material which is useful as a heterogeneous catalyst including the steps of: forming at least one copper oxide suspension comprising solid particles of copper oxide in a liquid; forming at least one carrier suspension comprising solid particles of a carrier material in a liquid; combining the copper oxide suspension and the carrier suspension; subjecting the combined suspensions to mechanical energy; separating the suspension liquid from the solid particles in the combined suspension; and subjecting the solid material to a thermal decomposition step. A catalyst made by the method has a BET surface area greater than 150 m$^2$/g, a particle size distribution in which D50 is in the range from 25-35 µm, and wherein the D50 after 60 minutes ultrasound treatment is at least 30% of the original value.

14 Claims, No Drawings

CATALYST AND METHOD OF MANUFACTURE

The invention concerns a manufacturing process for a catalyst and catalysts, especially copper-containing catalysts, made by the process.

Catalysts containing catalytically-active copper species have been commercially available and used in the chemicals industry for many years. Typical methods for making catalysts include the precipitation of the active catalytic compounds from a solution of soluble forms of the compounds and impregnation of soluble forms of active compounds onto inert carrier materials. Solid state manufacturing processes are also known in the art. U.S. Pat. No. 6,080,699 describes the manufacture of a catalyst in the form of solid particles solid particles and at least one carrier component in the form of solid particles wherein the components are dispersed in one another, wherein the inert component has a mean particle diameter greater than the mean particle diameter of the catalytically active component, and wherein the particles of the catalytically active material are grown on the particles of the carrier material. The catalyst material is combined whilst being subjected to ultrasound. WO90/09846 describes a heterogeneous catalyst containing one or more heavy and/or noble metals having a particle and crystallite size less than 50 nm which is obtained by mechanical alloying by means of grinding particles of material in a ball mill. We have found that the above processes can be improved to provide solid heterogeneous catalysts having enhanced performance.

According to the invention, we provide a preparation method for making a solid particulate material which is useful as a heterogeneous catalyst comprising the steps of:
(a) forming at least one copper oxide suspension comprising solid particles of copper oxide in a liquid;
(b) forming at least one carrier suspension comprising solid particles of a carrier material in a liquid;
(c) combining the copper oxide suspension and the carrier suspension;
(d) subjecting the combined suspensions to mechanical energy;
(e) separating the suspension liquid from the solid particles in the combined suspension; and
(f) subjecting the separated solid particles to a thermal decomposition step.

The resulting solid particulate material is an active copper catalyst which is useful for carrying our chemical reactions including hydrogenation, hydrogenolysis, (reductive) amination and dehydrogenation reactions. The catalyst is particularly useful for hydrogenation of carbonyl groups, e.g. for the production of fatty alcohols. The catalyst may be subjected to a reduction step to reduce at least some of the copper oxide to elemental copper. This reduction step may be carried out during the preparation of the catalyst or it may be done in the reactor in which the catalyst is to perform as a catalyst as a catalyst activation step. If the catalyst is to be reduced during its preparation then it may also be subjected to a further treatment such as a passivation or encapsulation, e.g. in a fatty or waxy substance, before supply to a user of the catalyst. Methods of passivation and encapsulation are well known in the art of catalyst manufacture.

We have found that it is preferable to make a catalyst using the above method without a granulation step and/or without a final grinding step to achieve a required particle size. A preferred method according to the invention consists essentially of steps (a)-(f). The method and catalyst of the invention differ from those described in U.S. Pat. No. 6,080,699 and the methods and catalysts described in that publication are explicitly disclaimed from the scope of this invention. In particular, the method of the present invention does not include a step of tableting, extruding, granulating or shaping the solid particles separated from the suspension in step (e).

The copper oxide suspension preferably comprises from 5-50% by weight of solid copper oxide particles. The carrier suspension preferably comprises from 5-50% by weight of solid carrier particles. The suspending liquid forming the suspensions of particles is preferably substantially aqueous, especially preferably water, optionally including compounds such as suspending agents, surfactants etc.

The mechanical energy in step (d) is preferably supplied by subjecting the combined suspension to a milling or grinding process. The terms "milling" and "grinding" are used to describe a mechanical process in which mechanical energy is applied to the suspensions in an amount which is greater than that required for mere mixing of the suspensions. The operations of milling and grinding each involve the application of mechanical energy such that a physical property of the solid particles of the suspension is changed as a result. The physical property which is changed by milling or grinding may include at least the average particle size and/or the shape of the particles. It is preferred that the mechanical energy applied to the combined suspensions is greater than 500 W/liter. By contrast, a mixing operation typically involves an energy input of from about 0.5 to 5 W/liter.

Following the mechanical process in step (d), the suspension liquid may be removed from the combined suspension in step (e) by various methods including filtration, decanting, or drying. It is particularly preferred to include a step of spray drying the combined suspension. The thermal decomposition step (f) is preferably a thermal treatment of the separated solid material at a temperature of at least 250° C., preferably at least 290° C. but less that 400° C., especially at a temperature between 300 and 350° C. The thermal treatment is preferably carried out in air or an alternative oxygen-containing gas.

According to the invention, we further provide a solid particulate catalyst comprising copper oxide and a solid carrier material, wherein said solid particulate catalyst is in the form of a powder having a BET surface area greater than 150 m$^2$/g, a particle size distribution in which D50 is in the range from 25-35 μm, and wherein the D50 after 60 minutes ultrasound treatment is at least 30% of the original value. The solid particulate catalyst of the invention may be obtained using the preparation method of the invention.

The catalyst comprises copper oxide and a solid carrier material. The carrier material used to form the suspension is typically a metal oxide. Preferred materials include silica-alumina, silica, alumina, zirconia, titania or other metal oxide materials that are commonly used as supports or diluents in catalyst manufacture. A particularly preferred material is silica-alumina.

In this specification, the D50 particle size values given represent the volume median particle size derived from measuring the particle size distribution using laser diffraction particle size analysis. D10 and D90 represent the particles size below which the particle size of 10% and 90% (respectively) of the measured particles fall. In this specification, values of D10 and D90 are also measured by laser diffraction. (D90−D10)/D50 is calculated from these values and can be used to represent the breadth of the distribution of particle sizes, such that a low value represents a narrower particle size distribution than a larger value. D50, D10 and D90 are standard terms used in the art of particle size analysis and can be measured using standard commercially-available particle size analysis apparatus.

The carrier material for use in the preparation method preferably has a D50 of between 10 and 50 µm, especially 20-40 µm. The copper oxide used in the preparation method to form the suspension typically has a D50 of between 10 and 100 µm, especially 30-60 µm.

The catalyst preferably comprises from 5% to 90% by weight of copper oxide, the remaining mass preferably consisting of the carrier material and optionally other materials.

The catalyst of the invention or made using the method of the invention has a BET surface area of at least 140 m$^2$/g, more preferably at least 150 m$^2$/g, and especially at least 160 m$^2$/g. The BET surface area is measured by nitrogen absorption at 77 K. The catalyst is a powder, having a particle size distribution in which D50 is in the range from 25-35 µm. Preferably the particle size distribution of the catalyst is sufficiently narrow so that (D90−D10)/D50 is not more than 1.4, especially not more than 1.3.

The catalyst of the invention has a D50 after ultrasound treatment for 60 minutes (indicated hereinafter as D50A) of at least 30% of the value before ultrasound treatment when measured using the attrition test described below. This is represented by 100*D50A/D50≥30. This is indicative of the resistance of the catalyst particles to attrition, with lower values showing that the median particle size has been reduced by the ultrasound to less than 30% of the original value. The resistance of the catalyst to attrition is important when the catalyst must be separated from the reaction mixture after it has been used in a reaction. When a catalyst is not sufficiently resistant to attrition the particles can break up during use in a chemical reaction process to produce finer particles which can be difficult to remove from the reaction mixture or product by filtration.

Attrition Test 500 ml demineralised water is recycled over a flow-through cell with ultrasound connection. 4 g solids are slowly added and homogenised for 5 min. Ultrasound is applied for 1 h at 500 W/liter. A 150 ml sample is taken every 15 min, 10 ml of which is consumed in the particle size analysis. The remainder is put back into the recycle.

EXAMPLE 1

A catalyst according to the invention was prepared according to the following method. 3 parts of a suspension containing 20% by weight of copper oxide powder (D50=45 µm) in water was combined with 2 parts of a suspension containing 20% by weight of silica-alumina powder (Siral-10, 90 wt % alumina, 10 wt % silica, Sasol Germany, D50=30 µm) in water.

The combined suspensions were milled in a stirrer bead mill (Fryma MS 32 using 1 mm zirconium silicate beads filling 75% of the volume) operating at 3000 rpm (27 kW input) and a throughput of 150 liters/hour over 8.5 hours. The milled suspension was then spray-dried to <2% moisture content in a rotary disc dryer operating at an inlet temperature of 300° C. and outlet temperature 90° C. The resulting solids were calcined in air at 320° C. to yield a material with a loss on ignition (800° C., 2 h) of <15%. The particle size distribution, measured using a Malvern Mastersizer laser diffraction apparatus, is shown in Table 1. The surface area was measured using the BET method of nitrogen adsorption at 77K.

COMPARATIVE EXAMPLE 2

3 Parts of a suspension containing 20% by weight of copper oxide powder (D50=45 µm) in water was combined with 2 parts of a suspension containing 20% by weight of silica alumina powder (Siral-10, 90 wt % alumina, 10 wt % silica, Sasol Germany, D50=30 µm) in water. The combined suspensions were milled in a stirrer bead mill (Fryma MS 32 using 1 mm zirconium silicate beads filling 75% of the volume) operating at 3000 rpm (27 kW input) and a throughput of 150 liters/hour over 8.5 hours. The milled suspension was then spray-dried in a rotary disc dryer operating at an inlet temperature of 300° C. and outlet temperature 90° C. to <2% moisture content. 10% demineralised water was added to the solids, and the solids were then further dried in a vacuum extruder (Händle, Type XC) at 10 to 20 mbar and a temperature range of 110 to 130° C. and formed into a granulate with a diameter of 2 mm. The resulting solids were calcined in air at 320° C. to yield a material with a loss on ignition (800 ° C., 2 h) of <15%and subsequently milled using a mortar grinder.

COMPARATIVE EXAMPLE 3

3 Parts of a suspension containing 20% by weight of copper oxide powder (D50=45 µm) in water was combined with 2 parts of a suspension containing 20% by weight of silica alumina powder (Siral-10, 90 wt % alumina, 10 wt % silica, Sasol Germany, D50=30 µm) in water. The combined suspensions were milled in a stirrer bead mill (Fryma MS 32 using 1 mm zirconium silicate beads filling 75% of the volume) operating at 3000 rpm (27 kW input) and a throughput of 150 liters/hour over 8.5 hours. The milled suspension was then spray-dried in a rotary disc dryer operating at an inlet temperature of 300° C. and outlet temperature 90° C. to <2% moisture content. 10% demineralised water was added to the solids, and the solids were then further dried in a vacuum extruder (Händle, Type XC) at 10 to 20 mbar and a temperature range of 110 to 130° C. and formed into a granulate with a diameter of 2 mm and subsequently milled using a mortar grinder.

COMPARATIVE EXAMPLE 4

5 Parts of a suspension containing 20% by weight of copper hydroxycarbonate powder (D50=50 µm, TIB Chemicals, ca 47% copper) in water was combined with 2 parts of a suspension containing 20% by weight of silica alumina powder (Siral-10, 90 wt % alumina, 10 wt % silica, Sasol Germany, D50=30 µm) in water. The combined suspensions were milled in a stirrer bead mill (Fryma MS 32 using 1 mm zirconium silicate beads filling 75% of the volume) operating at 3000 rpm (27 kW input) and a throughput of 150 liters/hour over 8.5 hours. The milled suspension was then spray-dried in a rotary disc dryer operating at an inlet temperature of 300° C. and outlet temperature 90° C. to <2% moisture content. The resulting solids were calcined in air at 320° C. to yield a material with a loss on ignition (800° C., 2 h) of <15%.

EXAMPLE 5

Activity Test 7 g of each of the catalysts made in Examples 1-4 was tested in the hydrogenation of 300g fatty C12-C18 methyl ester to alcohol in a 1 liter autoclave at 280° C. at 100 bar hydrogen pressure. The conversion after a reaction time of 30 minutes is shown in Table 1. A commercially available copper chromite catalyst was also tested as an additional comparison.

EXAMPLE 6

Attrition

A sample of each of the catalysts was tested using the attrition test described above. The particle size distribution (D50) after 60 minutes of this treatment (or, where shown, after only 30 minutes) is shown in Table 1 as "D50A". The attrition % is calculated as 100×((D50−D50A)/D50).

TABLE 1

|  | Example 1 | Comparative Example 2 | Comparative Example 3 | Comparative Example 4 | Comparative copper chromite |
|---|---|---|---|---|---|
| BET SA (m2/g) | 168 | 116.6 | 152 | 123.0 | 40 |
| D50 (μm) | 30 | 44.6 | 30 | 38.2 | 25 |
| D90 (μm) | 57.5 | 75.5 | 61.9 | 62.6 | 31.3 |
| D10 (μm) | 21.2 | 11.9 | 20.3 | 7.2 | 2.6 |
| (D90 − D10)/D50 | 1.21 | 1.43 | 1.39 | 1.45 | 1.15 |
| D50A (μm) after 60 min | 12.1 | 15 | 5.6 | After 30 min 3 | After 30 min 3 |
| Attrition % | 60 | 66 | 81 | 92 | 88 |
| Activity (% conversion) | 70 | 67.2 | 68.7 | 63.0 | 70 |

The invention claimed is:

1. A solid particulate catalyst comprising copper oxide and a solid carrier material, wherein said solid particulate catalyst is in the form of a powder having a BET surface area greater than 150 m$^2$/g, a particle size distribution in which D50 is in the range from 25-35 μm, and wherein the D50 after 60 minutes ultrasound treatment is at least 30% of the original value.

2. A solid particulate catalyst according to claim 1 which is obtainable by the preparation method of comprising the steps of:
   (a) forming at least one copper oxide suspension comprising solid particles of copper oxide in a liquid;
   (b) forming at least one carrier suspension comprising solid particles of a carrier material in a liquid;
   (c) combining the copper oxide suspension and the carrier suspension;
   (d) subjecting the combined suspensions to mechanical energy;
   (e) separating the suspension liquid from the solid particles in the combined suspension; and
   (f) subjecting the separated solid particles to a thermal decomposition step.

3. A solid particulate catalyst according to any claim 1, wherein the carrier material comprises a metal oxide.

4. A solid particulate catalyst according to claim 3, wherein the carrier material comprises silica-alumina, silica, alumina, zirconia or titania.

5. A method for making the solid particulate catalyst of claim 1 which is useful as a heterogeneous catalyst comprising the steps of:
   (a) forming at least one copper oxide suspension comprising solid particles of copper oxide in a liquid;
   (b) forming at least one carrier suspension comprising solid particles of a carrier material in a liquid;
   (c) combining the copper oxide suspension and the carrier suspension;
   (d) subjecting the combined suspensions to mechanical energy;
   (e) separating the suspension liquid from the solid particles in the combined suspension; and
   (f) subjecting the separated solid particles to a thermal decomposition step.

6. A method according to claim 5 consisting essentially of steps (a)-(f).

7. A method according to claim 5, wherein the material comprises from 5% to 90% by weight of copper oxide.

8. A method according to claim 5, wherein step (d) comprises subjecting the combined suspensions to a milling or grinding process.

9. A method according to claim 5, wherein in step (d) the mechanical energy applied to the combined suspensions is greater than 500 W/liter.

10. A method according to claim 5, wherein the carrier material comprises a metal oxide.

11. A method according to claim 10, wherein the carrier material comprises silica-alumina, silica, alumina, zirconia or titania.

12. A process for carrying out a chemical reaction selected from the type of reaction including hydrogenation, hydrogenolysis, amination and dehydrogenation, comprising adding a solid particulate catalyst according to claim 1 to a reaction mixture.

13. The process according to claim 12, wherein the reaction is for hydrogenation of carbonyl groups.

14. The process according to claim 13, wherein the reaction is for the production of a fatty alcohol.

* * * * *